(12) United States Patent
Ishida et al.

(10) Patent No.: US 6,706,208 B2
(45) Date of Patent: Mar. 16, 2004

(54) STABILIZED HYDROXYALKYL (METH)ACRYLATE

(75) Inventors: Tokumasa Ishida, Himeji (JP); Yasuhiro Shingai, Himeji (JP); Masatoshi Ueoka, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 651 days.

(21) Appl. No.: 09/728,179

(22) Filed: Dec. 1, 2000

(65) Prior Publication Data

US 2001/0006226 A1 Jul. 5, 2001

(30) Foreign Application Priority Data

Dec. 22, 1999  (JP) ............................. 11-365154

(51) Int. Cl.⁷ .............................. C09K 3/00; C08K 5/13

(52) U.S. Cl. .......................... 252/182.29; 252/182.28; 252/182.13

(58) Field of Search ................. 252/182.29, 182.24, 252/182.28, 182.13

(56) References Cited

U.S. PATENT DOCUMENTS

| | | | |
|---|---|---|---|
| 3,399,229 A | | 8/1968 | Kunze et al. |
| 3,804,884 A | | 4/1974 | Jeffrey et al. |
| 4,049,731 A | * | 9/1977 | Restaino .......................... 585/3 |
| 4,198,238 A | * | 4/1980 | Scheve .................... 430/286.1 |
| 4,368,320 A | * | 1/1983 | Aldinger et al. ............. 528/355 |
| 4,757,098 A | * | 7/1988 | Merrem et al. ................ 522/75 |
| 5,126,396 A | * | 6/1992 | Orton et al. ................... 525/28 |
| 5,258,423 A | * | 11/1993 | Crabb et al. ................. 523/206 |
| 6,102,205 A | * | 8/2000 | Greff et al. .................. 206/438 |
| 6,528,601 B1 | * | 3/2003 | Hara et al. ................... 526/256 |

FOREIGN PATENT DOCUMENTS

| | | |
|---|---|---|
| EP | 0 620 206 A1 | 10/1994 |
| GB | 1400978 | 7/1975 |
| JP | 48-78119 | 10/1973 |
| JP | 58-46496 B2 | 10/1983 |

* cited by examiner

*Primary Examiner*—Joseph D. Anthony
(74) *Attorney, Agent, or Firm*—Haugen Law Firm PLLP

(57) ABSTRACT

To sufficiently stabilize a hydroxyalkyl (meth)acrylate in spite of its easily polymerizable property, a hydroxyalkyl saturated-carboxylate and/or alkylene glycol as well as a phenol compound is added thereto.

8 Claims, No Drawings

STABILIZED HYDROXYALKYL (METH)ACRYLATE

BACKGROUND OF THE INVENTION

A. Technical Field

The present invention relates to a stabilized hydroxyalkyl (meth)acrylate.

B. Background Art

Hydroxyalkyl (meth)acrylate is very high in reactivity and is easily polymerized, and hence it is general to stabilize hydroxyalkyl (meth)acrylate by adding polymerization inhibitor in its manufacturing process, storage or transportation. As the polymerization inhibitor, hitherto, various compounds have been used, including phenol compounds such as hydroquinone, methyl hydroquinone, tert-butyl hydroquinone, 2,6-di-tert-butyl parahydroquinone, 2,5-di-tert-butyl hydroquinone, 2,4-dimethyl-6-tert-butyl phenol, and hydroquinone monomethyl ether, or para-phenylene diamines such as N-isopropyl-N'-phenyl-para-phenylene diamine, N-(1,3-dimethyl butyl)-N'-phenyl-para-phenylene diamine, N-(1-methyl heptyl)-N'-phenyl-para-phenylene diamine, N,N'-diphenyl-para-phenylene diamine, and N,N'-di-2-naphthyl-para-phenylene diamine, or amines such as thiodiphenylamine.

However, as mentioned above, hydroxyalkyl (meth) acrylate is very likely to be polymerized. Usually, products of hydroxyalkyl (meth)acrylate contain impurities, including water, alkylene chlorohydrin, alkylene glycol di(meth) acrylate, dialkylene glycol mono(meth)acrylate, dialkylene glycol di(meth)acrylate, trialkylene glycol mono(meth) acrylate, trialkylene glycol di(meth)acrylate, (meth)acrylic acid dimer, hydroxyalkyl-β-acryloyloxy propionate, dialkylene glycol-β-acryloyloxy propionate, reaction materials such as (meth)acrylic acid and alkylene oxide, and others, in a range of several ppm to several percent, and they act to promote polymerization of hydroxyalkyl (meth)acrylate. Owing to these reasons, if the conventional polymerization inhibitors as listed above are used in stabilization of hydroxyalkyl (meth)acrylate, the polymerization inhibitory effects were not sufficient. It causes problems not only in the storage and transportation process, but also in the manufacturing process of hydroxyalkyl (meth)acrylate, in particular, and if polymerization takes place in the course of operation, pipings are clogged and the productivity is lowered, which leads to a tremendous economical loss.

SUMMARY OF THE INVENTION

A. Object of the Invention

Accordingly, an object of the present invention is to sufficiently stabilize the hydroxyalkyl (meth)acrylate in spite of its easily polymerizable property.

B. Disclosure of the Invention

The present inventors diligently studied to solve the above problems. As a result, the inventors have completed the present invention by finding that, by adding a specific ester compound and/or glycol compound to the phenol compound hitherto used as polymerization inhibitor, the stabilizing effect upon the easily polymerizable hydroxyalkyl (meth) acrylate is considerably enhanced as compared with conventional cases.

That is to say, a stabilized hydroxyalkyl (meth)acrylate, according to the present invention, contains a hydroxyalkyl saturated-carboxylate and/or alkylene glycol along with a phenol compound.

These and other objects and the advantages of the present invention will be more fully apparent from the following detailed disclosure.

DETAILED DESCRIPTION OF THE INVENTION

Stabilizing Method

The present invention is characterized by achieving the stabilization of the hydroxyalkyl (meth)acrylate by using the hydroxyalkyl saturated-carboxylate and/or alkylene glycol jointly with the phenol compound.

The phenol compound used in the present invention is a phenol compound conventionally and generally used as polymerization inhibitor, and preferable examples thereof include hydroquinone, methyl hydroquinone, tert-butyl hydroquinone, 2,6-di-tert-butyl parahydroquinone, 2,5-di-tert-butyl hydroquinone, 2,4-dimethyl-6-tert-butyl phenol, and hydroquinone monomethyl ether. These may be used either alone respectively or in combinations with each other.

The hydroxyalkyl saturated-carboxylate and/or alkylene glycol used together with the phenol compound in the present invention is a compound which characterizes the technical concept of the present invention. Examples of the hydroxyalkyl saturated-carboxylate preferably include hydroxyethyl acetate, hydroxyethyl propionate, hydroxyethyl isobutyrate, hydroxypropyl acetate, hydroxypropyl propionate, and hydroxypropyl isobutyrate. These may be used either alone respectively or in combinations with each other. As the alkylene glycol, preferably, ethylene glycol, propylene glycol and others may be used. These may also be used either alone respectively or in combinations with each other.

In the present invention, the amount of the phenol compound as used is preferably in the range of 0.001 to 0.5 wt % of hydroxyalkyl (meth)acrylate, and preferably 0.005 to 0.1 wt %. If less than 0.001 wt %, the polymerization inhibitory effect is not enough, or if more than 0.5 wt %, it is not economical.

In the present invention, the amount of the hydroxyalkyl saturated-carboxylate and/or alkylene glycol as used is preferably in the range of 0.0001 to 2 wt %, more preferably 0.001 to 2 wt %, and still more preferably 0.01 to 1 wt %, of hydroxyalkyl (meth)acrylate. If less than 0.0001 wt %, the polymerization inhibitory effect is not enough, or if more than 2 wt %, it is not economical.

In the present invention, the mixing rate of hydroxyalkyl saturated-carboxylate and/or alkylene glycol to phenol compound is not particularly limited, and each should be contained at the above rate in the hydroxyalkyl (meth)acrylate, and the blending rate by weight of the hydroxyalkyl saturated-carboxylate and/or alkylene glycol to the phenol compound is preferably in the range of 0.1 to 100 times, more preferably 1 to 80 times. If less than 0.1 times or more than 100 times, it is not preferred because the feature of the present invention, that is, the synergistic effect by combined use of hydroxyalkyl saturated-carboxylate and/or alkylene glycol with phenol compound is decreased.

In the present invention, the compound to be combined with the phenol compound is hydroxyalkyl saturated-carboxylate and/or alkylene glycol, and by either compound, the stabilizing effect of the present invention is sufficiently exhibited, and in particular the hydroxyalkyl saturated-carboxylate tends to have a higher stabilizing effect than the alkylene glycol.

In the present invention, the hydroxyalkyl saturated-carboxylate and/or alkylene glycol as well as the phenol compound is allowed to coexist with the hydroxyalkyl (meth)acrylate, but, if aromatic hydrocarbon and/or aliphatic hydrocarbon is also allowed to coexist with the hydroxyalkyl (meth)acrylate, the polymerization inhibitory effect upon hydroxyalkyl (meth)acrylate is enhanced. The aromatic hydrocarbon is not particularly limited, but is preferably at least one member selected from the group consisting of benzene, toluene, and xylene. The aliphatic hydrocarbon is not particularly limited, but is preferably at least one member selected from the group consisting of hexane, heptane, and octane. In the case where the aromatic hydrocarbon and/or aliphatic hydrocarbon is also allowed to coexist with the hydroxyalkyl (meth)acrylate, the amount of the aromatic hydrocarbon and/or aliphatic hydrocarbon as added is preferably in the range of 0.0001 to 1 wt %, more preferably 0.0001 to 0.1 wt %, of hydroxyalkyl (meth) acrylate. If less than 0.0001 wt %, the polymerization inhibitory effect is not enough, or if more than 1 wt %, it is not economical.

In the present invention, the method of adding phenol compound, hydroxyalkyl saturated-carboxylate and/or alkylene glycol, and, if necessary, aromatic hydrocarbon and/or aliphatic hydrocarbon, for stabilization of hydroxyalkyl (meth)acrylate is not particularly limited, but, for example, in the manufacturing process of hydroxyalkyl (meth) acrylate, they may be added together with the raw materials, or may be added in the distillation tower in the refining process. Or, by a method of adding saturated carboxylic acid corresponding to hydroxyalkyl saturated-carboxylate, for example, acetic acid, propionic acid, or isobutyric acid, at the time of reaction, hydroxyalkyl saturated-carboxylate may be formed in the reaction solution, or by adding water at the time of reaction, alkylene glycol may be produced. It is also possible to add preliminarily before storage or transportation of hydroxyalkyl (meth)acrylate. The phenol compound, hydroxyalkyl saturated-carboxylate and/or alkylene glycol, and, if necessary, aromatic hydrocarbon and/or aliphatic hydrocarbon may be either added simultaneously, or added independently.

Incidentally, in the present invention, when adding phenol compound and hydroxyalkyl saturated-carboxylate and/or alkylene glycol, in the manufacturing process of hydroxyalkyl (meth)acrylate, together with the raw materials at the time of reaction, or adding in the distillation tower in the refining process, depending on the thermal condition at the time of reaction or distillation, hydroxyalkyl saturated-carboxylate may be hydrolyzed or alkylene glycol may be dehydrated between molecules. In such a case, the process solution in the manufacturing process for hydroxyalkyl (meth)acrylate, for example, the reaction solution, distillation bottom liquid, distillate, or product may be lowered in concentration of hydroxyalkyl saturated-carboxylate and/or alkylene glycol in the process solution, and the feature of the present invention, that is, the synergistic effect by combined use of hydroxyalkyl saturated-carboxylate and/or alkylene glycol with phenol compound is not expressed, and sufficient stabilizing effect is not expected. It is hence necessary to check, in the analysis of the process solution, the concentration of hydroxyalkyl saturated-carboxylate and/or alkylene glycol remaining in the reaction solution, distillation bottom liquid, distillate and product of hydroxyalkyl (meth)acrylate undergoing thermal condition, and to supply the hydroxyalkyl saturated-carboxylate and/or alkylene glycol in the specified range of the present invention if the concentration is found to be lowered. In this case, examples of the method for analyzing the concentration of the remaining hydroxyalkyl saturated-carboxylate and/or alkylene glycol include analysis by GC (gas chromatography).

Stabilizing Agent

In execution of the present invention, the following stabilizing agent may be preferably used. This stabilizing agent contains the hydroxyalkyl saturated-carboxylate and/or alkylene glycol along with the phenol compound, and is preferably used in the present invention.

The phenol compound used in the stabilizing agent is, same as mentioned above, the phenol compound generally used hitherto as polymerization inhibitor, preferably including hydroquinone, methyl hydroquinone, tert-butyl hydroquinone, 2,6-di-tert-butyl parahydroquinone, 2,5-di-tert-butyl hydroquinone, 2,4-dimethyl-6-tert-butyl phenol, and hydroquinone monomethyl ether. These may be used either alone respectively or in combinations with each other. The hydroxyalkyl saturated-carboxylate usable in the stabilizing agent preferably includes, same as mentioned above, hydroxyethyl acetate, hydroxyethyl propionate, hydroxyethyl isobutyrate, hydroxypropyl acetate, hydroxypropyl propionate, and hydroxypropyl isobutyrate. These may be used either alone respectively or in combinations with each other. The alkylene glycol usable in the stabilizing agent preferably includes, same as mentioned above, ethylene glycol and propylene glycol. These may also be used either alone respectively or in combinations with each other.

The stabilizing agent comprises phenol compound and hydroxyalkyl saturated-carboxylate and/or alkylene glycol and is used to stabilize the hydroxyalkyl (meth)acrylate, and the blending rate of the hydroxyalkyl saturated-carboxylate and/or alkylene glycol to the phenol compound is preferably in the range of 0.1 to 100 times, more preferably 1 to 80 times, by weight. If less than 0.1 times or more than 100 times, it is not preferred because the feature of the present invention, that is, the synergistic effect by combined use of hydroxyalkyl saturated-carboxylate and/or alkylene glycol with phenol compound is decreased.

The stabilizing agent contains both phenol compound and hydroxyalkyl saturated-carboxylate and/or alkylene glycol and, if the phenol compound are mixed with hydroxyalkyl saturated-carboxylate and/or alkylene glycol in the above rate, the content of each component in the stabilizing agent is not particularly limited, but is preferably as follows: the content of the phenol compound is in the range of 0.1 to 90.0 wt %, and the content of the hydroxyalkyl saturated-carboxylate and/or alkylene glycol is in the range of 1.0 to 99.9 wt %, and the content of other additives is in the range of 0 to 90.0 wt %. When the rate of hydroxyalkyl saturated-carboxylate and/or alkylene glycol to phenol compound is out of the above range, the synergistic effect by combined use of phenol compound with hydroxyalkyl saturated-carboxylate and/or alkylene glycol is not expressed, and sufficient stabilizing effect is not expected.

As is mentioned above, the stabilizing agent may further contain other additives, as required, in addition to phenol compound and hydroxyalkyl saturated-carboxylate and/or alkylene glycol. Other additives include, for example, phenothiazine, or para-phenylene diamines such as N-isopropyl-N'-phenyl-para-phenylene diamine, N-(1,3-dimethyl butyl)-N'-phenyl-para-phenylene diamine, N-(1-methyl heptyl)-N'-phenyl-para-phenylene diamine, N,N'-diphenyl-para-phenylene diamine, and N,N'-di-2-naphthyl-para-phenylene diamine, or amine compounds such as thiodiphenylamine, or copper dialkyl dithiocarbamates such as copper dibutyl dithiocarbamate, copper diethyl dithiocarbamate, and copper dimethyl dithiocarbamate, or nitroso compounds such as nitrosodiphenyl amine, isoamyl nitrite, N-nitroso-cyclohexyl hydroxylamine, and N-nitroso-N-phenyl-N-hydroxyl amine, or N-oxyl compounds such as 2,2,4,4-tetramethyl azetidine-1-oxyl, 2,2-dimethyl-4,4-dipropyl azetidine-1-oxyl, 2,2,5,5-tetramethyl pyrrolidine-1-oxyl, 2,2,5,5-tetramethyl-3-oxopyrrolidine-1-oxyl, 2,2,6,6-tetramethyl piperidine-1-oxyl, 4-hydroxy-2,2,6,6- tetramethyl piperidine-1-oxyl, 6-aza-7,7-dimethyl-spiro(4, 5) decane-6-oxyl, 2,2,6,6-tetramethyl-4-acetoxy piperidine-1-oxyl, and 2,2,6,6-tetramethyl-4-benzoyloxy piperidine-1-oxyl, but are not limited them alone.

The stabilizing agent may further contain aromatic hydrocarbon and/or aliphatic hydrocarbon in addition to phenol compound and hydroxyalkyl saturated-carboxylate and/or alkylene glycol. By this coexistence, the polymerization inhibitory effect upon hydroxyalkyl (meth)acrylate is enhanced. The aromatic hydrocarbon is not particularly limited, but is preferably at least one member selected from the group consisting of benzene, toluene, and xylene. The aliphatic hydrocarbon is not particularly limited, but is preferably at least one member selected from the group consisting of hexane, heptane, and octane. In the case where the stabilizing agent further contains the aromatic hydrocarbon and/or aliphatic hydrocarbon, the rate of the aromatic hydrocarbon and/or aliphatic hydrocarbon to the phenol compound is preferably in the range of 0.0001 to 10 times, preferably 0.0001 to 1 times. If less than 0.0001 times or more than 10 times, the synergistic effect by combined use of the aromatic hydrocarbon and/or aliphatic hydrocarbon is less, which is not preferred.

Effects and Advantages of the Invention

The present invention can sufficiently stabilize the hydroxyalkyl (meth)acrylate in spite of its easily polymerizable property.

DETAILED DESCRIPTION OF THE PREFERRED EMBODIMENTS

Hereinafter, the present invention is more specifically illustrated by the following examples of some preferred embodiments in comparison with comparative examples not according to the invention. However, the invention is not limited to these examples.

The hydroxyethyl acrylate used in the examples is a refined product from which the stabilizing agent has been removed.

EXAMPLE 1

First, 100 g of hydroxyethyl acrylate was placed into a glass container, and then 0.03 g of hydroquinone monomethyl ether and 0.1 g of hydroxyethyl acetate were added. Immediately after this addition, the container was immersed into an oil bath as adjusted to 100° C., and the time to initiate a polymerization was measured, but the polymerization did not occur even after 130 hours.

EXAMPLE 2

First, 100 g of hydroxyethyl acrylate was placed into a glass container, and then 0.03 g of hydroquinone monomethyl ether and 0.05 g of ethylene glycol were added. Immediately after this addition, the container was immersed into an oil bath as adjusted to 100° C., and the time to initiate a polymerization was measured. As a result, popcorn polymerization of hydroxyethyl acrylate in the container was not observed until 125 hours passed.

EXAMPLE 3

First, 100 g of hydroxyethyl acrylate was placed into a glass container, and then 0.03 g of hydroquinone monomethyl ether and 0.01 g of hydroxyethyl acetate were added. Immediately after this addition, the container was immersed into an oil bath as adjusted to 100° C., and the time to initiate a polymerization was measured. As a result, popcorn polymerization of hydroxyethyl acrylate in the container was not observed until 100 hours passed.

EXAMPLE 4

First, 100 g of hydroxyethyl acrylate was placed into a glass container, and then 0.03 g of hydroquinone monomethyl ether, 0.01 g of hydroxyethyl acetate, and 0.1 g of toluene were added. Immediately after this addition, the container was immersed into an oil bath as adjusted to 100° C., and the time to initiate a polymerization was measured. As a result, popcorn polymerization of hydroxyethyl acrylate in the container was not observed until 119 hours passed.

EXAMPLE 5

First, 100 g of hydroxyethyl acrylate was placed into a glass container, and then 0.03 g of hydroquinone monomethyl ether and 1.0 g of hydroxyethyl acetate were added. Immediately after this addition, the container was immersed into an oil bath as adjusted to 90° C., and the time to initiate a polymerization was measured, but the polymerization did not occur even after 500 hours.

EXAMPLE 6

First, 100 g of hydroxyethyl acrylate was placed into a glass container, and then 0.03 g of hydroquinone monomethyl ether and 0.5 g of hydroxyethyl acetate were added. Immediately after this addition, the container was immersed into an oil bath as adjusted to 90° C., and the time to initiate a polymerization was measured. As a result, popcorn polymerization of hydroxyethyl acrylate in the container was not observed until 402 hours passed.

Comparative Example 1

First, 100 g of hydroxyethyl acrylate was placed into a glass container, and then 0.03 g of hydroquinone monomethyl ether was added. Immediately after this addition, the container was immersed into an oil bath as adjusted to 100° C., and the time to initiate a polymerization was measured. As a result, popcorn polymerization of hydroxyethyl acrylate in the container was observed after only 65 hours.

Comparative Example 2

First, 100 g of hydroxyethyl acrylate was placed into a glass container, and then 0.1 g of hydroxyethyl acetate was added. Immediately after this addition, the container was immersed into an oil bath as adjusted to 100° C., and the time to initiate a polymerization was measured. As a result, popcorn polymerization of hydroxyethyl acrylate in the container was observed after only 16 hours.

Comparative Example 3

First, 100 g of hydroxyethyl acrylate was placed into a glass container, and then 0.03 g of phenothiazine and 0.1 g of hydroxyethyl acetate was added. Immediately after this addition, the container was immersed into an oil bath as adjusted to 100° C., and the time to initiate a polymerization was measured. As a result, popcorn polymerization of hydroxyethyl acrylate in the container was observed after only 73 hours.

Comparative Example 4

First, 100 g of hydroxyethyl acrylate was placed into a glass container, and then 0.03 g of hydroquinone monomethyl ether was added. Immediately after this addition, the container was immersed into an oil bath as adjusted to 90° C., and the time to initiate a polymerization was measured. As a result, popcorn polymerization of hydroxyethyl acrylate in the container was observed after 235 hours.

Comparative Example 5

First, 100 g of hydroxyethyl acrylate was placed into a glass container, and then 0.5 g of hydroxyethyl acetate was added. Immediately after this addition, the container was immersed into an oil bath as adjusted to 90° C., and the time to initiate a polymerization was measured. As a result, popcorn polymerization of hydroxyethyl acrylate in the container was observed after only 38 hours.

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A stabilized hydroxyalkyl acrylate or hydroxyalkyl methacrylate, which comprises a hydroxyalkyl saturated-carboxylate and/or alkylene glycol along with a polymerization inhibiting phenol compound.

2. A stabilized hydroxyalkyl acrylate or hydroxyalkyl methacrylate according to claim 1, which further comprises an aromatic hydrocarbon and/or aliphatic hydrocarbon.

3. A stabilized hydroxyalkyl acrylate or hydroxyalkyl methacrylate according to claim 1, wherein the hydroxyalkyl saturated-carboxylate is at least one member selected from the group consisting of hydroxyethyl acetate, hydroxyethyl propionate, hydroxyethyl isobutyrate, hydroxypropyl acetate, hydroxypropyl propionate, and hydroxypropyl isobutyrate.

4. A stabilized hydroxyalkyl acrylate or hydroxyalkyl methacrylate according to claim 3, which further comprises an aromatic hydrocarbon and/or aliphatic hydrocarbon.

5. A stabilized hydroxyalkyl acrylate or hydroxyalkyl methacrylate according to claim 1, wherein the alkylene glycol is at least one member selected from the group consisting of ethylene glycol and propylene glycol.

6. A stabilized hydroxyalkyl acrylate or hydroxyalkyl methacrylate according to claim 5, which further comprises an aromatic hydrocarbon and/or aliphatic hydrocarbon.

7. A stabilized hydroxyalkyl acrylate or hydroxyalkyl methacrylate according to claim 3, wherein the alkylene glycol is at least one member selected from the group consisting of ethylene glycol and propylene glycol.

8. A stabilized hydroxyalkyl acrylate or hydroxyalkyl methacrylate according to claim 7, which further comprises an aromatic hydrocarbon and/or aliphatic hydrocarbon.

* * * * *